US00PP30852P2

(12) United States Plant Patent
Roberts et al.

(10) Patent No.: US PP30,852 P2
(45) Date of Patent: Aug. 27, 2019

(54) ***VITEX* PLANT NAMED 'BAILTEXTWO'**

(50) Latin Name: *Vitex agnus-castus*
Varietal Denomination: Bailtextwo

(71) Applicant: Bailey Nurseries Inc, Newport, MN (US)

(72) Inventors: David Roberts, Athens, GA (US); Rhonda Helvick, Madison, GA (US); Oren McBee, Bishop, GA (US)

(73) Assignee: BAILEY NURSERIES, INC., Newport, MN (US)

( * ) Notice: Subject to any disclaimer, the term of this patent is extended or adjusted under 35 U.S.C. 154(b) by 0 days.

(21) Appl. No.: 15/999,885

(22) Filed: Aug. 27, 2018

(51) Int. Cl.
*A01H 5/00* (2018.01)
*A01H 6/50* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Vitex* plant named 'Bailtextwo' that is characterized by its compact and rounded to upright habit, its prolific flowering habit that produces flowers that are vibrant purple-pink in color, its freely branched habit and its excellent vigor.

2 Drawing Sheets

Botanical classification: *Vitex agnus-castus*.
Variety denomination: 'Bailtextwo'.

BACKGROUND OF THE INVENTION

The present invention relates to a new and distinct cultivar of *Vitex agnus-castus*. The new *Vitex* will hereafter be referred to by its cultivar name, 'Bailtextwo'. 'Bailtextwo' is a new cultivar of *Vitex agnus-castus* grown for use as an ornamental landscape plant.

The new cultivar was derived from a controlled breeding program conducted by the Inventors in Watkinsville, Ga. 'Bailtextwo' arose from open pollination of *Vitex agnus-castus* 'Flora Ann' (not patented) as the female parent. The male parent is therefore unknown. 'Bailtextwo' was selected as a single unique plant from the progeny of the open-pollination in 2015 after evaluation for growth habit, foliage, and flower characteristics.

Asexual propagation of the new cultivar was first accomplished by semi-hardwood stem cuttings by one of the Inventors in Watkinsville, Ga. in 2015. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. The attributes in combination distinguish 'Bailtextwo' as a unique cultivar of *Vitex*.

1. 'Bailtextwo' exhibits a compact and rounded to upright habit.
2. 'Bailtextwo' exhibits a prolific flowering habit that produces flowers that are vibrant purple-pink in color.
3. 'Bailtextwo' exhibits a freely branched habit.
4. 'Bailtextwo' exhibits excellent vigor.

The female parent plant differs from 'Bailtextwo' in having flowers that are less vibrant in color, flower stalks that are shorter in height and in being less vigorous. 'Bailtextwo' can be most closely compared to *Vitex agnus-castus* cultivars 'V07-SC-OP-4' (U.S. Plant Pat. No. 27,374) and 'PIIVAC-1' (U.S. Plant Pat. No. 25,914). 'V07-SC-OP-4' differs from 'Bailtextwo' in having flower stalks that are shorter in height, a less vigorous growth habit, a smaller plant size, and a more compact plant habit. 'PIIVAC-1' differs from 'Bailtextwo' in having flowers that are purple in color and darker green foliage.

BRIEF DESCRIPTION OF THE DRAWINGS

The accompanying colored photographs illustrate the overall appearance and distinct characteristics of the new *Vitex*. The photographs in the figures were taken of a plant 3 years in age as grown in a trial garden in Watkinsville, Ga.

The photograph in FIG. 1 provides a side view of a plant of 'Bailtextwo' in bloom.

Figure 1:
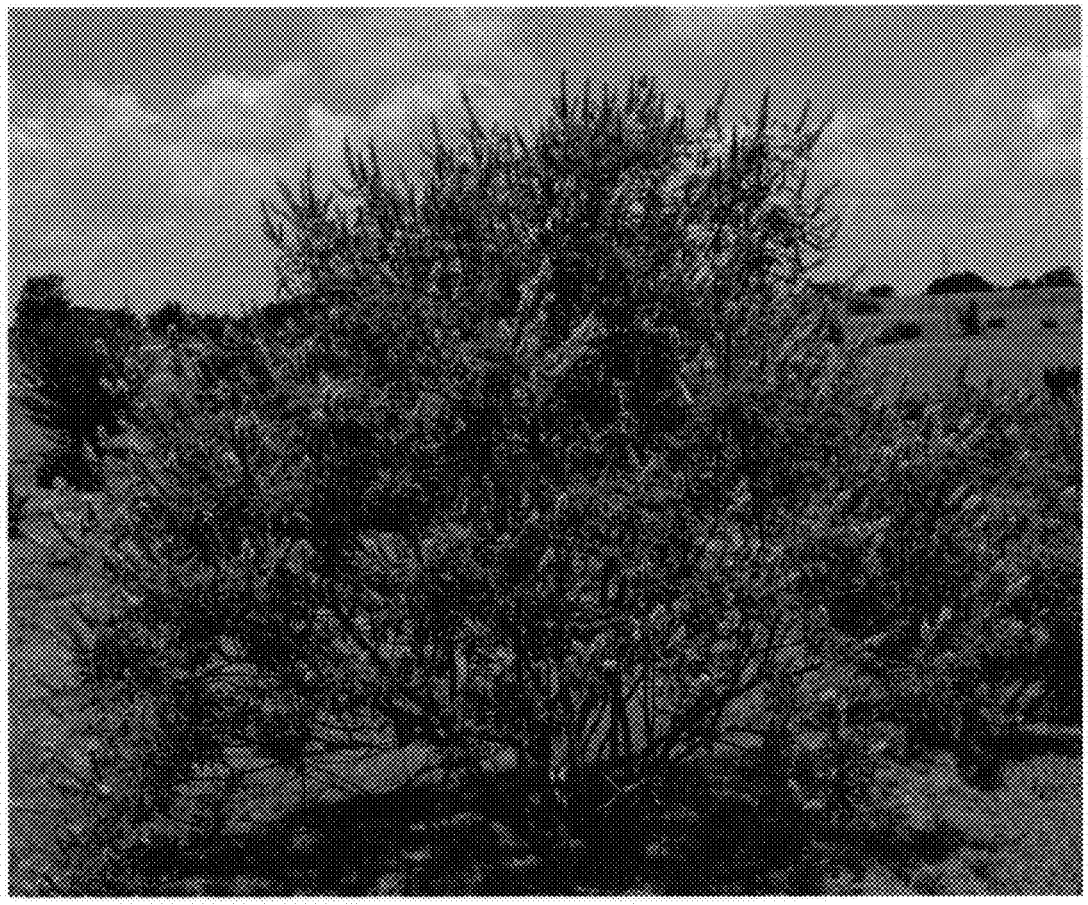
Figure 2:
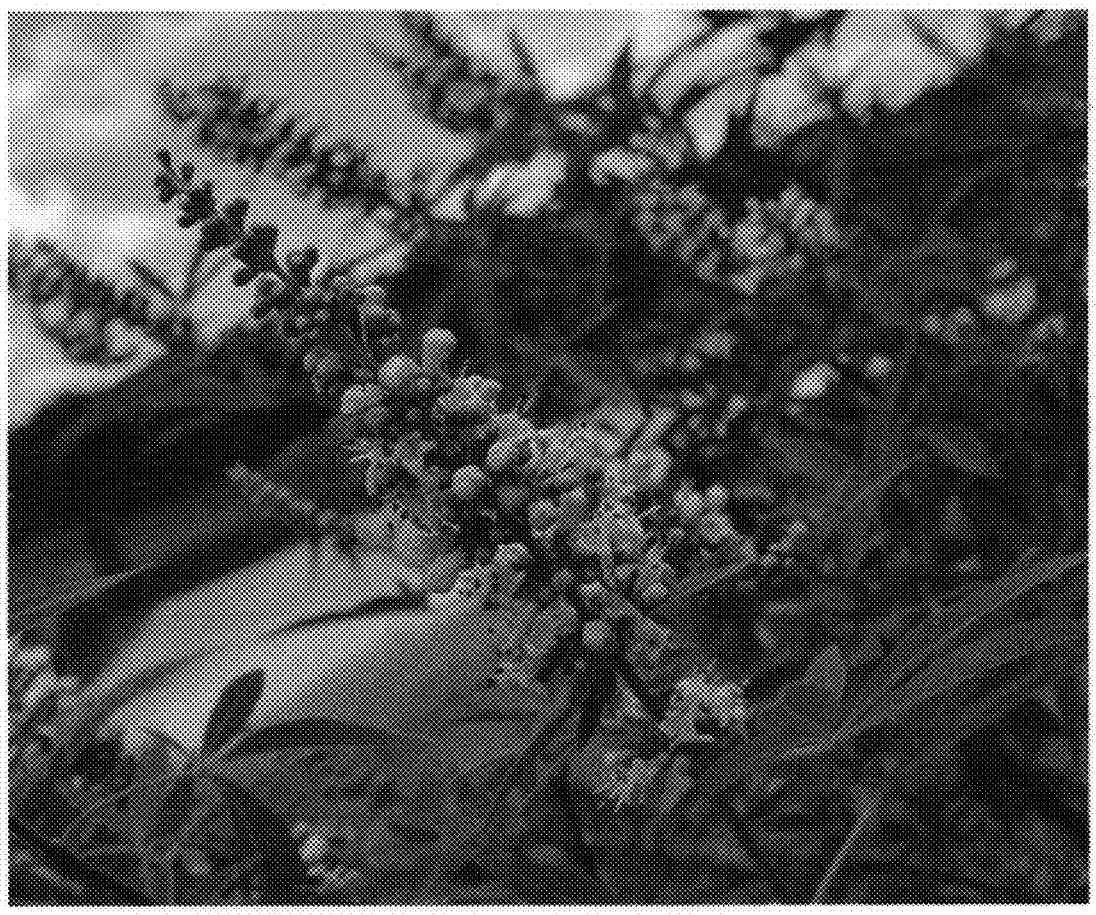

The photograph in HG. 2 provides a close-up view of the flowers of 'Bailtextwo'.

The colors in the photographs are as close as possible with the digital photography and printing techniques utilized and the color codes in the detailed botanical description accurately describe the colors of the new *Vitex*.

DETAILED BOTANICAL DESCRIPTION

The following is a detailed description of plants 3-years in age as grown in a trial garden in Watkinsville, Ga. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—June to September in Watkinsville, Ga.

*Plant type*.—Deciduous flowering shrub.

*Plant habit*.—Compact and rounded to upright plant habit.

*Height and spread*.—An average of 2.03 m in height and 2.66 m in width as a 3-year-old plant in the landscape.

*Hardiness*.—U.S.D.A. Zones 7 to 9.

*Diseases and pests*.—Similar susceptibility and resistance to diseases and pests as other cultivars of *Vitex* has been observed.

*Root description*.—156A in color, young roots are fibrous, older roots become woody.

*Propagation*.—Semi-hardwood stem cuttings.

*Root development*.—An average of 6 weeks at 32° C. for root initiation and an average of 3 months at 32° C. to produce a young rooted plant.

*Growth rate*.—Vigorous.

Branch description:

*Branch strength*.—Young; flexible and strong, mature; easily broken.

*Branch aspect*.—Held at angles ranging between 45° and 75°.

*Branch shape*.—Tetragonal on first year growth and round on second year growth.

*Branch color*.—Main and lateral branches; first year color N199A, flushed with 56A, second year color 200C, trunk 200C.

*Branch surface*.—Main and lateral branches; first year covered with tomentulose pubescence, second year glabrous, trunk fine barked.

*Branching habit*.—Freely and multi-branching habit, pruning enhances lateral development an average of 15 lateral branches on a 3 year-old plant.

*Internode length*.—Average of 6 cm.

*Vegetative buds*.—Opposite in arrangement, sessile, average of 1.5 mm in length and 1 mm in width, subglobose in shape, N199A in color, surface has 2 bud scales covered with tomentulose pubescence.

Foliage description:

*Leaf number*.—An average of 25 per branch.

*Leaf arrangement*.—Opposite, palmate.

*Leaf shape*.—Whole leaf; ovate, leaflet; elliptic to ovate to lanceolate.

*Leaf size*.—Whole leaf; 6 cm in length, 11 cm in width, leaflet; 6 cm in length, 2 cm in width.

*Leaf division*.—Compound with 3 to 5 leaflets.

*Leaflet base*.—Cuneate.

*Leaflet apex*.—Acuminate.

*Leaflet margin*.—Entire.

*Leaflet venation*.—Pinnate, upper surface N144A, lower surface 138D.

*Leaflet attachment*.—Petiolate.

*Leaflet surface*.—Upper surface glabrous and glossy, lower surface tomentulose.

*Leaf color*.—Young upper surface; 138A, young lower surface; 138B, mature upper surface; 137B, mature lower surface; 146A.

*Foliage fragrance*.—A spicy aroma when crushed.

*Petioles*.—Average of 3 cm in length and 2 mm in diameter, both surfaces tomentulose, 191A in color with a hint of 56A on upper surface.

*Petiolules*.—Average of 1 cm in length and 1.5 mm in width, both surfaces tomentulose, 191A in color with a hint of 56A on upper surface.

Flower description:

*Inflorescence type*.—Terminal racemose-panicle.

*Inflorescence size*.—An average of 15 cm in height and 6 cm in width.

*Lastingness of inflorescence*.—Inflorescences are showy for an average of 2 weeks, individual flowers last an average of 2 days, self-cleaning.

*Inflorescence quantity*.—25 to 30 per lateral branch.

*Fragrance*.—Very faint.

*Quantity of flowers*.—An average of 250 flowers per inflorescence.

*Flower type*.—Bilabiate (one larger petal and one 4-lobed).

*Flower size*.—An average of 1 cm in height and 5 mm in diameter.

*Flower buds*.—Obovate in shape, average of 8 mm in length, 4 mm in depth, surface is glabrous, 143B in color.

*Flower aspect*.—Upright to outward.

*Pedicel*.—Strong, an average of 5 mm in length and 1 mm in diameter 199B in color, surface is tometulose.

*Peduncle*.—Strong, an average of 5 cm in length and 2.5 mm in diameter, 199B in color, surface is glabrous.

*Petals*.—An average of 2, fused at the base to form the corolla tube, tube; an average of 4 mm in length and 2 mm in width, 68B in color on both surfaces, lower petal; cupped, 5 mm in length, 3 mm in width, oblong shape, broad obtuse to rounded apex, upper and lower surface glabrous, entire margin, upper petal; 4-lobed, each 3 mm in length, 2.5 mm in width, oblong in shape, broad obtuse to rounded apex, upper and lower surface glabrous, entire margin color both petals; upper surface 68B, lower surface 65C.

*Calyx*.—Consists of 5 fused sepals with acute apices, an average of 5 mm in length and 2 mm in diameter.

*Sepals*.—An average of 5 in a single whorl, fused at the base, elliptical in shape, entire margins, acute apex, both surfaces are tometulose, an average of 5 mm in length and 2 mm in width, outer surface 191B in color, inner surface N144B in color.

Reproductive organs:

*Gynoecium*.—Pistil; 1 inferior, an average of 3 mm in length, 1 mm in width, glabrous surface, style; an average of 3 mm in length and 69D in color, stigma; forked, 1 mm in width and 155C in color, ovary; 155C in color and 1 mm in diameter.

*Androecium*.—Stamens; 4 per flower attached to the inner base of the corolla tube, 4 mm in length, glabrous surface, anther; 59A in color, filaments; 56D in color, pollen; is moderate in quantity and 155B in color.

*Fruit and seed*.—Drupe, rounded to oblong in shape, average of 4 mm in length, 3 mm in diameter, immature color; N144B at the base and 63A at the apex, mature color; N200D, each drupe contains one seed that is about 3.5 mm in length, 2.5 mm in width and N199B in color.

It is claimed:

1. A new and distinct cultivar of *Vitex* plant named 'Bailtextwo' as herein illustrated and described.

* * * * *